US012655099B2

(12) United States Patent
Xu et al.

(10) Patent No.: US 12,655,099 B2
(45) Date of Patent: Jun. 16, 2026

(54) SUBSTITUTED PHENYL SULFIDE COMPOUND AND APPLICATION THEREOF

(71) Applicants: SHENYANG SINOCHEM AGROCHEMICALS R&D CO., LTD., Shenyang (CN); JIANGSU YANGNONG CHEMICAL CO., LTD., Yangzhou (CN)

(72) Inventors: Libao Xu, Shenyang (CN); Hongfei Wu, Shenyang (CN); Xiuhui Chang, Shenyang (CN); Haibo Yu, Shenyang (CN); Yuquan Song, Shenyang (CN); Jingbo Xu, Shenyang (CN); Chunxiao Guo, Shenyang (CN); Xueming Cheng, Shenyang (CN); Ningning Sun, Shenyang (CN)

(73) Assignees: SHENYANG SINOCHEM AGROCHEMICALS R&D CO., LTD., Shenyang (CN); JIANGSU YANGNONG CHEMICAL CO., LTD., Yangzhou (CN)

( * ) Notice: Subject to any disclaimer, the term of this patent is extended or adjusted under 35 U.S.C. 154(b) by 574 days.

(21) Appl. No.: 18/005,572

(22) PCT Filed: Jul. 13, 2021

(86) PCT No.: PCT/CN2021/105866

§ 371 (c)(1),
(2) Date: Jan. 13, 2023

(87) PCT Pub. No.: WO2022/012483

PCT Pub. Date: Jan. 20, 2022

(65) Prior Publication Data

US 2023/0271919 A1 Aug. 31, 2023

(30) Foreign Application Priority Data

Jul. 17, 2020 (CN) ........................ 202010690160.9

(51) Int. Cl.

| | |
|---|---|
| *C07C 323/62* | (2006.01) |
| *A01N 37/34* | (2006.01) |
| *A01N 37/36* | (2006.01) |
| *A01P 7/02* | (2006.01) |
| *C07C 317/32* | (2006.01) |
| *C07C 323/09* | (2006.01) |
| *C07C 323/65* | (2006.01) |

(52) U.S. Cl.

CPC ............ *C07C 323/62* (2013.01); *A01N 37/34* (2013.01); *A01N 37/36* (2013.01); *A01P 7/02* (2021.08); *C07C 317/32* (2013.01); *C07C 323/09* (2013.01); *C07C 323/65* (2013.01)

(58) Field of Classification Search

CPC ... C07C 317/14; C07C 317/32; C07C 323/09; C07C 323/62; C07C 323/65; A01N 31/08; A01N 33/18; A01N 37/34; A01N 41/10; A01N 37/36

See application file for complete search history.

(56) References Cited

U.S. PATENT DOCUMENTS 6,509,354 B1 * 1/2003 Toriyabe ................ A01N 43/76 544/298

FOREIGN PATENT DOCUMENTS

| | | | |
|---|---|---|---|
| CN | 105541682 | A | 5/2016 |
| CN | 111100048 | A | 5/2020 |
| CN | 111100049 | A | 5/2020 |
| CN | 111226927 | A | 6/2020 |
| CN | 111226955 | A | 6/2020 |
| JP | 2009023910 | A | 2/2009 |
| WO | 9955668 | A1 | 11/1999 |
| WO | 2006013048 | A1 | 2/2006 |
| WO | 2013027660 | A1 | 2/2013 |
| WO | 2014202505 | A1 | 12/2014 |
| WO | 2017067500 | A1 | 4/2017 |

* cited by examiner

*Primary Examiner* — John Pak

(74) *Attorney, Agent, or Firm* — NKL Law; Allen Xue

(57) ABSTRACT

The present invention belongs to the field of agricultural acaricides, and particularly relates to a substituted phenyl sulfide compound and an application thereof. The substituted phenyl sulfide compound is as represented in general formula I. Definitions of substituted groups in the formula are given in the description. The compound of the general formula I has excellent acaricidal activity and can be used for preventing and controlling various mites.

I

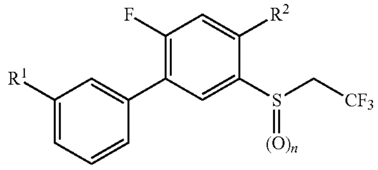

9 Claims, No Drawings

SUBSTITUTED PHENYL SULFIDE COMPOUND AND APPLICATION THEREOF

TECHNICAL FIELD

The present invention belongs to the field of agricultural acaricides, and particularly relates to substituted phenyl sulfide compounds and applications thereof.

BACKGROUND ART

In recent years, due to the long-term uses of the existing acaricides, the pest mites have been induced to generate serious resistance. It is necessary to constantly develop more efficient novel acaricidal compounds and compositions. At the same time, with the growing demand for agricultural and livestock products and the increasing emphasis on environmental protection, there is always a need to use novel acaricides which are low in cost and friendly to the environment.

Patent WO9955668 discloses compounds KC1, KC2, and KC3 (compounds I-238, I-358 and I-599, respectively in WO9955668) which have lethal activity of more than 90% against two-spotted spider mites at a concentration of 500 ppm. Patent WO2013027660 discloses a compound KC4 (compound 2-557 in WO2013027660) which has lethal activity of more than 90% against two-spotted spider mites at a concentration of 50 ppm. These disclosed compounds have certain acaricidal activity, but the acaricidal activity is not satisfactory at low doses.

KC1

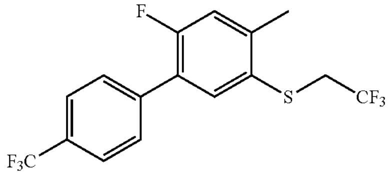

KC2

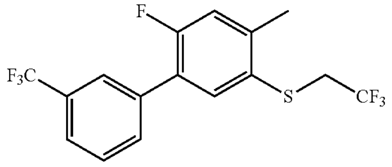

KC3

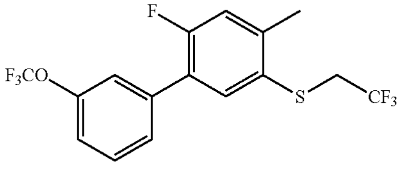

KC4

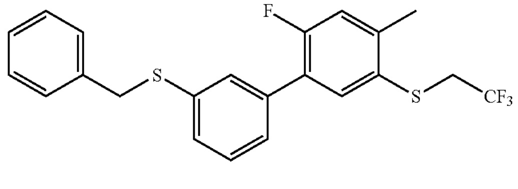

SUMMARY OF THE INVENTION

The purpose of the present invention is to provide novel substituted phenyl sulfide compounds which can be applied to the control of mites in the fields of agriculture, forestry and public health.

To achieve the above purpose, the technical solution of the present invention is as follows:

A substituted phenyl sulfide compound is shown in general formula I:

I

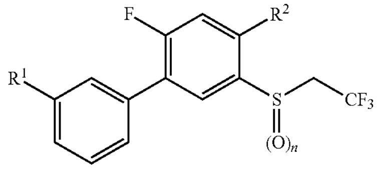

wherein:

$R^1$ is selected from nitro, cyano, $C_1$-$C_4$ alkylthio, trifluoromethanesulfonyl or $SCH_2CF_3$;

$R^2$ is selected from halogen, cyano or $C_1$-$C_4$ alkyl;

n is selected from 0, 1 or 2.

A preferred compound in the present invention is shown in the general formula I, wherein:

$R^1$ is selected from nitro, cyano, $C_1$-$C_4$ alkylthio, trifluoromethanesulfonyl or $SCH_2CF_3$;

$R^2$ is selected from fluorine, chlorine or methyl;

n is selected from 0 or 1.

A further preferred compound in the present invention is shown in the general formula I, wherein:

$R^1$ is selected from nitro, cyano, methylthio, ethylthio or $SCH_2CF_3$;

$R^2$ is selected from chlorine or methyl;

n is selected from 0 or 1.

A more preferred compound in the present invention is shown in the general formula I, wherein:

$R^1$ is selected from nitro, cyano, methylthio, ethylthio or $SCH_2CF_3$;

$R^2$ is selected from methyl;

n is selected from 0 or 1.

A most preferred compound in the present invention is shown in the general formula I, wherein:

$R^1$ is selected from nitro, methylthio or $SCH_2CF_3$;

$R^2$ is selected from methyl;

n is selected from 0 or 1.

A use of the compound of the general formula I as an acaricide in the fields of agriculture, forestry or public health is provided.

The compound of the general formula I can be used as an acaricide in the fields of agriculture, forestry and public health at a concentration of 500-0.3 ppm under laboratory conditions.

An acaricidal composition comprises the compound of the general formula I and an agriculturally acceptable carrier. The compound of the general formula I is taken as an active component, and the weight percentage of the active component in the composition is 0.1-99%.

In the above definitions of the compounds of the general formula I, the terms used in the collection generally represent the following substituents:

Halogen refers to fluorine, chlorine, bromine or iodine.

Alkyl refers to linear or branched alkyl, such as methyl, ethyl, n-propyl, isopropyl or different butyl, pentyl or hexyl isomers.

Alkylthio refers to linear or branched alkyl, which is bonded to the structure through a sulfur atom, such as methylthio and ethylthio.

The following methods can be used to prepare the compounds of the general formula I in the present invention, but not to limit the preparation methods of these compounds. In the reaction formula, unless otherwise stated, the definitions of the groups are the same as above.

Method I:

The compound of general formula I can be prepared by the reaction of the compound of general formula II with the compound of general formula III under the action of a metal catalyst in an appropriate solvent and under alkaline conditions.

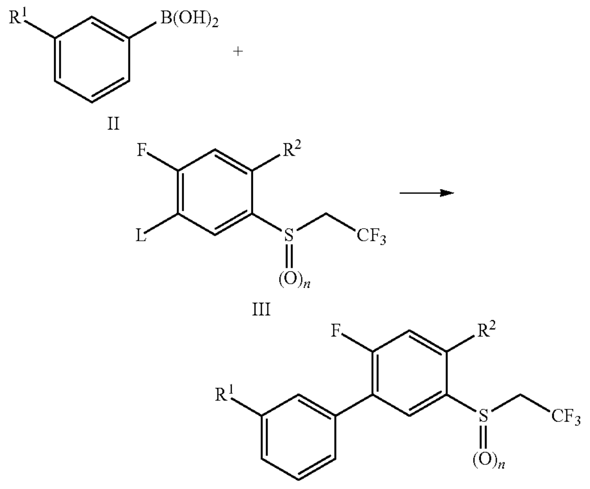
II
III
I

Reaction solvents can be selected from ethyl ether, tetrahydrofuran, dioxane, ethylene glycol dimethyl ether, acetonitrile, DMF, ethyl acetate, benzene, methanol, ethanol, water or a mixture thereof. The alkali used in the reaction can be selected from sodium hydroxide, potassium hydroxide, sodium carbonate, potassium carbonate, sodium bicarbonate, potassium bicarbonate, sodium hydroxide, sodium alcohol or organic base like triethylaamine. The metal catalyst can be selected from palladium on carbon, palladium acetate, tetrakis(triphenylphosphine)palladium, 1,1'-bis (diphenylphosphino) ferrocene-palladium (II) dichloride dichloromethane complex, bis (triphenylphosphine) nickel chloride or tetrakis(triphenylphosphine)nickel, etc. In the formula, L represents halogen or trifluoromethanesulfonyloxy group.

Method II:

The compound of general formula I can also be prepared by the compound of general formula IV and the compound of general formula V under the action of a metal catalyst in an appropriate solvent and under alkaline conditions.

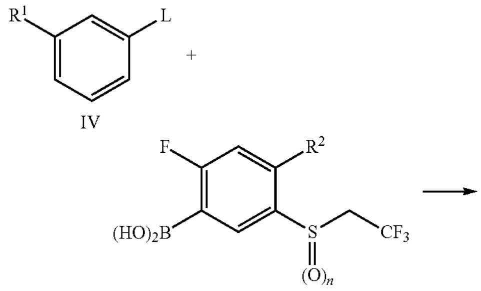
IV
V

-continued

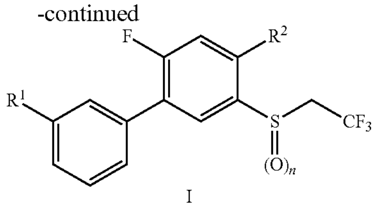
I

The solvents, alkalis and metal catalysts used in the reaction can be referred to method I. In the formula, L represents halogen or trifluoromethanesulfonyloxy group.

Method III:

The compound of general formula I can also be prepared by the reaction of the compound of general formula I-a with an appropriate oxidant (n is 1 or 2).

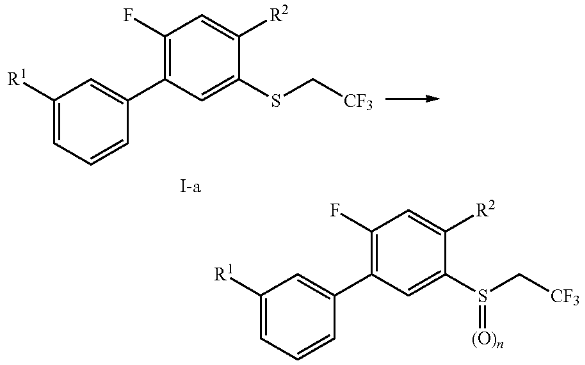
I-a
I

The appropriate oxidant in the reaction can be selected from hydrogen peroxide, sodium periodate or 3-chloroperoxybenzoic acid. The reaction solvents are mainly selected from dichloromethane, chloroform, methanol, ethanol, acetic acid, tetrahydrofuran, dioxane, ethyl acetate, DMF, water or a mixture thereof.

The sources of the compounds involved in the above preparation methods may be commercially available raw materials or prepared by the methods known in the field.

The compound of the general formula III can be prepared by referring to the methods disclosed in WO2006013048, WO2014202505 and WO2017067500, and the compound of the general formula V can be prepared by referring to the methods disclosed in JP2009023910 and WO2014202505.

The specific compounds listed in Table 1 can be used to illustrate the present invention, but not to limit the present invention.

TABLE 1

I

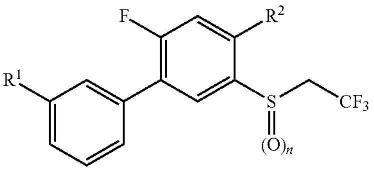

| Compound | $R^1$ | $R^2$ | n |
|---|---|---|---|
| 1 | CN | $CH_3$ | 0 |
| 2 | CN | $CH_3$ | 1 |

TABLE 1-continued

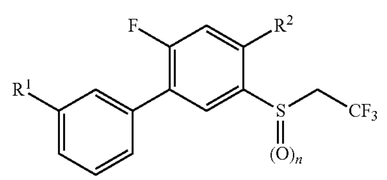

I

| Compound | $R^1$ | $R^2$ | n |
|---|---|---|---|
| 3 | CN | Cl | 0 |
| 4 | CN | Cl | 1 |
| 5 | $NO_2$ | $CH_3$ | 0 |
| 6 | $NO_2$ | $CH_3$ | 1 |
| 7 | $NO_2$ | F | 0 |
| 8 | $NO_2$ | Cl | 0 |
| 9 | $NO_2$ | Cl | 1 |
| 10 | $NO_2$ | CN | 0 |
| 11 | $SO_2CF_3$ | $CH_3$ | 0 |
| 12 | $SO_2CF_3$ | $CH_3$ | 1 |
| 13 | $SO_2CF_3$ | Cl | 0 |
| 14 | $SCH_3$ | $CH_3$ | 0 |
| 15 | $SCH_3$ | $CH_3$ | 1 |
| 16 | $SCH_3$ | Cl | 0 |
| 17 | $SCH_2CH_3$ | $CH_3$ | 0 |
| 18 | $SCH_2CH_3$ | $CH_3$ | 1 |
| 19 | $SCH_2CF_3$ | $CH_3$ | 0 |
| 20 | $SCH_2CF_3$ | $CH_3$ | 1 |
| 21 | $SCH_2CF_3$ | Cl | 0 |
| 22 | $SCH_2(CH_3)_2$ | $CH_3$ | 0 |

The substituted phenyl sulfide compound of the present invention has excellent acaricidal activity, so the present invention further comprises the use of the compound of the general formula I for controlling harmful mites.

The examples of the mites mentioned below are only used to illustrate the present invention, but not to limit the present invention.

*Acari* (mites): *Eriophyes* spp., such as *Phyllocoptruta oleivora* and *Aculus schlechtendali; Steneotarsonemus* spp., such as *Polyphagotarsonemus latus; Tenuipalpus* spp., such as *Brevipalpus phoenicis; Tetranychus* spp., such as *Tetranychus cinnabarinus, Tetranychus Kanzawai Kishida, Tetranychus pacificus*, Cotton spider mites, *Tetranychus urticae koch, Panonychus ulmi* and *Tetranychus citrus.*

In particular, the compound of the general formula I of the present invention has unexpected high activity against adult mites, nymph mites, larva mites and mite eggs. Meanwhile, the compound of the general formula I has low toxicity to many beneficial insects and mites, mammals, fish and birds, and has no phytotoxicity.

Due to the positive characteristics, the above compounds can be advantageously used to protect important crops, livestock and breeding stock in agriculture and horticulture, and to avoid the damage of pest mites to the environment that humans often go to.

For practical application in agriculture, it is generally beneficial to use a composition containing one or more compounds of the general formula I.

Therefore, another technical solution of the present invention also comprises an acaricidal composition, wherein the composition comprises the compound of the general formula I and an agriculturally acceptable carrier. The compound of the general formula I is taken as an active component, and the weight percentage of the active component in the composition is 0.1-99%.

It should be clear that various changes and modifications can be made within the scope defined by the claims of the present invention.

DETAILED DESCRIPTION

The following specific embodiments are used to further illustrate the present invention, but the present invention is not limited to these examples.

Synthesis Embodiments

Embodiment 1: Preparation of Compound 1

3-Cyanophenylboronic acid (1.47 g, 10.0 mmol), 2-fluoro-4-methyl-5-trifluoroethylthio bromobenzene (3.00 g, 10.0 mmol), 1,1'-bis (diphenylphosphino) ferrocene-palladium (II) dichloride dichloromethane complex (0.1 g) and potassium carbonate (2 g) were added to a 100 ml three-necked flask. Then a mixed solution of ethylene glycol dimethyl ether (20 ml) and water (10 ml) was added. The reaction mixture was heated at reflux for 4 hours under stirring, and the reaction was monitored by TLC. After completion of the reaction, the mixture was cooled to room temperature, and was diluted with water and extracted with ethyl acetate. The organic layer was washed with saturated brine, dried over anhydrous magnesium sulfate, filtered, and concentrated under reduced pressure; and the residue was purified by column chromatography to obtain white solid (2.60 g). $^1H$ NMR (600 MHz, $CDCl_3$) δ (ppm): 7.80 (s, 1H), 7.74-7.72 (m, 1H), 7.66-7.65 (m, 1H), 7.60 (d, 1H), 7.55 (t, 1H), 7.10 (d, 1H), 3.35 (q, 2H), 2.54 (s, 3H).

Embodiment 2: Preparation of Compound 5

3-Nitrophenylboronic acid (1.67 g, 10.0 mmol), 2-fluoro-4-methyl-5-trifluoroethylthio bromobenzene (3.00 g, 10.0 mmol), 1,1'-bis (diphenylphosphino) ferrocene-palladium (II) dichloride dichloromethane complex (0.1 g) and potassium carbonate (2 g) were added to a 100 ml three-necked flask. Then a mixed solution of ethylene glycol dimethyl ether (20 ml) and water (10 ml) was added. The reaction mixture was heated at reflux for 4 hours under stirring, and the reaction was monitored by TLC. After completion of the reaction, the mixture was cooled to room temperature, and was diluted with water and extracted with ethyl acetate. The organic layer was washed with saturated brine, dried over anhydrous magnesium sulfate, filtered, and concentrated under reduced pressure; and the residue was purified by column chromatography to obtain pale yellow solid (2.80 g). $^1H$ NMR (600 MHz, $CDCl_3$) δ (ppm): 8.39 (s, 1H), 8.25-8.23 (m, 1H), 7.86-7.84 (m, 1H), 7.66 (d, 1H), 7.63 (t, 1H), 7.12 (d, 1H), 3.36 (q, 2H), 2.55 (s, 3H).

Embodiment 3: Preparation of Compound 6

Compound 5 (0.35 g, 1.0 mmol) was added to a flask with chloroform (10 ml), and then 3-chloroperoxybenzoic acid (0.25 g, 1.0 mmol, content of 70-75%) was added in an ice water bath. The reaction mixture was stirred for 2 hours, and diluted with chloroform, washed with aqueous sodium thiosulfate solution and aqueous sodium bicarbonate solution in sequence. The organic layer was dried over anhydrous magnesium sulfate, filtered, and concentrated under reduced pressure; and the residue was purified by column chromatography to obtain white solid (0.31 g). $^1H$ NMR (600 MHz, $CDCl_3$) δ (ppm): 8.46 (s, 1H), 8.29-8.27 (m, 1H), 8.10 (d, 1H), 7.92-7.90 (m, 1H), 7.66 (t, 1H), 7.16 (d, 1H), 3.54-3.45 (m, 2H), 2.37 (s, 3H).

Embodiment 4: Preparation of Compound 14

3-(Methylthio)phenylboronic acid (1.68 g, 10.0 mmol), 2-fluoro-4-methyl-5-trifluoroethylthio bromobenzene (3.00 g, 10.0 mmol), 1,1'-bis (diphenylphosphino) ferrocene-palladium (II) dichloride dichloromethane complex (0.1 g) and potassium carbonate (2 g) were added to a 100 ml three-necked flask. Then a mixed solution of ethylene glycol dimethyl ether (20 ml) and water (10 ml) was added. The reaction mixture was heated at reflux for 4 hours under stirring, and the reaction was monitored by TLC. After completion of the reaction, the mixture was cooled to room temperature, and was diluted with water and extracted with ethyl acetate. The organic layer was washed with saturated brine, dried over anhydrous magnesium sulfate, filtered, and concentrated under reduced pressure; and the residue was purified by column chromatography to obtain an oil (2.75 g). $^1$H NMR (600 MHz, $CDCl_3$) δ (ppm): 7.61 (d, 1H), 7.39-7.34 (m, 2H), 7.28-7.26 (m, 2H), 7.05 (d, 1H), 3.34 (q, 2H), 2.52-2.50 (m, 6H).

Embodiment 5: Preparation of Compound 17

3-(Ethylthio)phenylboronic acid (1.82 g, 10.0 mmol), 2-fluoro-4-methyl-5-trifluoroethylthio bromobenzene (3.00 g, 10.0 mmol), 1,1'-bis (diphenylphosphino) ferrocene-palladium (II) dichloride dichloromethane complex (0.1 g) and potassium carbonate (2 g) were added to a 100 ml three-necked flask. Then a mixed solution of ethylene glycol dimethyl ether (20 ml) and water (10 ml) was added. The reaction mixture was heated at reflux for 4 hours under stirring, and the reaction was monitored by TLC. After completion of the reaction, the mixture was cooled to room temperature, and was diluted with water and extracted with ethyl acetate. The organic layer was washed with saturated brine, dried over anhydrous magnesium sulfate, filtered, and concentrated under reduced pressure; and the residue was purified by column chromatography to obtain an oil (2.80 g). $^1$H NMR (600 MHz, $CDCl_3$) δ (ppm): 7.61 (d, 1H), 7.45 (m, 1H), 7.37-7.30 (m, 3H), 7.05 (d, 1H), 3.34 (q, 2H), 2.99 (q, 2H), 2.52 (s, 3H), 1.35 (t, 3H).

Embodiment 6: Preparation of Compound 19

3-(2,2,2-Trifluoroethylthio)phenylboronic acid (2.36 g, 10.0 mmol), 2-fluoro-4-methyl-5-trifluoroethylthio bromobenzene (3.00 g, 10.0 mmol), 1,1'-bis (diphenylphosphino) ferrocene-palladium (II) dichloride dichloromethane complex (0.1 g) and potassium carbonate (2 g) were added to a 100 ml three-necked flask. Then a mixed solution of ethylene glycol dimethyl ether (20 ml) and water (10 ml) was added. The reaction mixture was heated at reflux for 4 hours under stirring, and the reaction was monitored by TLC. After completion of the reaction, the mixture was cooled to room temperature, and was diluted with water and extracted with ethyl acetate. The organic layer was washed with saturated brine, dried over anhydrous magnesium sulfate, filtered, and concentrated under reduced pressure; and the residue was purified by column chromatography to obtain an oil (3.10 g). $^1$H NMR (600 MHz, $CDCl_3$) δ (ppm): 7.64-7.63 (m, 1H), 7.61 (d, 1H), 7.51-7.48 (m, 1H), 7.46-7.40 (m, 2H), 7.07 (d, 1H), 3.49 (q, 2H), 3.34 (q, 2H), 2.53 (s, 3H).

Determination of Biological Activity

Embodiment 7: Determination of Activity Against Adult Spider Mite(*Tetranychus cinnabarinus*)

According to the solubility of test compounds, the compounds were dissolved with acetone or dimethyl sulfoxide, and then diluted with 0.1% aqueous solution of Tween 80 to form 50 ml test liquid and the content of the acetone or the dimethyl sulfoxide in the total solution was not more than 10% for later use. The adult spider mites were put into two true leaves of bean plants. After the number of mites were investigated, the solution of certain concentrations of test compounds was sprayed by using a handheld Airbrush. Three replicates were set for each treatment. Then the leaves were maintained in standard observation room. After 72 h, the number of surviving mites were observed, and the mortality rate was calculated.

Among some of the testing compounds, compounds 1, 2, 3, 5, 6, 8, 9, 11, 14, 17 and 19 showed better control effects against adult spider mites at a concentration of 10 mg/L, and the mortality was greater than 90%.

Among some of the testing compounds, compounds 1, 5, 6 and 14 showed better control effects against adult spider mites at a concentration of 5 mg/L, and the mortality was greater than 90%.

According to the above test method, compounds 5, 6 and 8 as well as compounds KC1, KC2, KC3, KC4, KC5 and KC6 were selected for parallel determination of activity against adult spider mites. See Table 2 for test results.

TABLE 2

| | Mortality (%) | |
|---|---|---|
| Compound | 1.25 mg/L | 0.625 mg/L |
| 5 | 100 | 95.5 |
| 6 | 97.6 | 80.6 |
| 8 | 90.7 | 65.2 |
| KC1 | 36.5 | — |
| KC2 | 56.6 | — |
| KC3 | 50.7 | — |
| KC4 | 16.4 | — |
| KC5 | 71.7 | 29.8 |
| KC6 | 0 | — |

KC5 and KC6 are comparative compounds prepared by replacing 3-cyanophenylboronic acid with p-nitrophenylboronic acid and o-nitrophenylboronic acid respectively according to the method of synthesis embodiment 1. The physical property data of KC5: $^1$H NMR (600 MHz, $CDCl_3$) δ (ppm): 8.30 (d, 2H), 7.68 (d, 2H), 7.65 (d, 1H), 7.10 (d, 1H), 3.35 (q, 2H), 2.54 (s, 3H); The physical property data of KC6: $^1$H NMR (600 MHz, $CDCl_3$) δ (ppm): 8.04 (d, 1H), 7.69-8.66 (m, 1H), 7.57-7.54 (m, 1H), 7.52 (d, 1H), 7.40 (d, 1H), 7.02 (d, 1H), 3.34 (q, 2H), 2.53 (s, 3H). The specific structure is as follows.

KC5

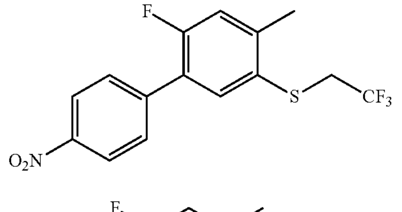

KC6

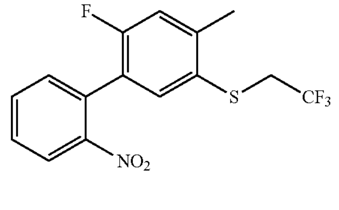

Embodiment 8: Determination of Activity Against Egg of Spider Mite (*Tetranychus Cinnabarinus*)

According to the solubility of test compounds, the compounds were dissolved with acetone or dimethyl sulfoxide, and then diluted with 0.1% aqueous solution of Tween 80 to form 50 ml test liquid and the content of the acetone or the dimethyl sulfoxide in the total solution was not more than 10% for later use. The leaves of bean were chopped into leaf discs and put into a petri dish. Female adult mites were inoculated. After laying eggs, the female adult mites were removed. After the number of eggs were investigated, the solution of certain concentrations of test compounds were sprayed with a POTTER spray tower, for 2 mL per treatment, and blank control was set. When all eggs in the blank control were incubated, the number of eggs which were incubated and unincubated was recorded, and incubation inhibition rate of the eggs was calculated.

Among some of the testing compounds, compounds 1, 5, 6, 11, 14, 17 and 19 showed better control effects against spider mite eggs at a concentration of 10 mg/L, and the mortality was greater than 90%.

Among some of the testing compounds, compounds 5, 6, 14 and 19 showed better control effects against spider mite eggs at a concentration of 5 mg/L, and the mortality was greater than 90%.

According to the above test method, compounds 5, 14 and 19 as well as known compounds KC1, KC2, KC3 and KC4 were selected for parallel determination of activity against spider mite eggs. See Table 3 for test results.

TABLE 3

| | Inhibition Rate (%) | |
|---|---|---|
| Compound | 1.25 mg/L | 0.625 mg/L |
| 5 | 100 | 100 |
| 14 | 95.8 | 65.3 |
| 19 | 81.1 | 51.2 |
| KC1 | 26.2 | — |
| KC2 | 36.7 | — |
| KC3 | 20.7 | — |
| KC4 | 40.8 | — |

Embodiment 9: Biological Activity for Controlling *Panonychus ulmi* (Field Trial)

The trial was carried out in the orchard of Research Institute of Pomology of Chinese Academy of Agricultural Sciences. The test sample was Starkrimson apple tree, which was 14 years old and the intervals between two plants was 2×4 m. The test compound 14 was set at two different doses of 50 mg/L and 100 mg/L, and Spirodiclofen suspension agent as the positive control was set at one dose of 50 mg/L. The test method was spraying by using the stretcher power sprayer, each treatment repeated three times. The number of initial mites was investigated before spraying, and the number of surviving mites was checked and recorded. The number of surviving mites was investigated on the 3 days, 7 days, 14 days and 21 days after spraying respectively. The decline rate of mite population was counted and the control efficiency was calculated.

$$\text{Control efficiency (\%)} = \left(1 - \frac{\text{number of mites before } CK \text{ treatment} \times \text{number of mites after pesticide application}}{\text{number of mites after } CK \text{ treatment} \times \text{number of mites before pesticide application}}\right) \times 100$$

The field trial results for compound 14 against *Panonychus ulmi* (Xingcheng, Liaoning, May, 2018) were shown in Table 4.Table 4

TABLE 4

| | | Control efficiency (%) | | | |
|---|---|---|---|---|---|
| Compound | Concentration (mg/L) | 3 days after pesticide application | 7 days after pesticide application | 14 days after pesticideg application | 21 days after pesticide application |
| 14 | 50 | 92.2 | 86.4 | 97.3 | 93.2 |
| | 100 | 94.4 | 96.6 | 99.8 | 99.1 |
| Spirodiclofen | 50 | 49.6 | 45.8 | 90.3 | 94.9 |

Embodiment 10: Biological Activity Against *Panonychus citri* (Field Trial)

The trial was carried out in the citrus orchard in Yibin City, Sichuan Province. The test sample was "Dekopon". The test citrus trees were 4 years old and the planting density was more than 70 plants/mu. The test compounds 6 and 14 were set at two different doses of 50 mg/L and 100 mg/L.

As the positive controls, Spirodiclofen suspension agent was set at one dose of 100 mg/L, and Pyridaben wettable powder was set at one dose of 100 mg/L. The test method was spraying by using Pentium 3WBD-20 sprayer, each treatment repeated three times. The number of initial mites was investigated before spraying, and the number of surviving mites was checked and recorded. The number of surviving mites was investigated on the 3 days, 7 days, 14 days, 21 days and 30 days after spraying respectively. The decline rate of mite populationg was counted and the control efficiency was calculated.

$$\text{Control efficiency (\%)} = \left(1 - \frac{\text{number of mites before } CK \text{ treatment} \times \text{number of mites after pesticide application}}{\text{number of mites after } CK \text{ treatment} \times \text{number of mites before pesticide application}}\right) \times 100$$

The field trial results for compound 6 and 14 against *Panonychus citri* (Yibin, Sichuan, September, 2019) were shown in Table 5.

TABLE 5

| | | Control efficiency (%) | | | | |
|---|---|---|---|---|---|---|
| Compound | Concentration (mg/L) | 3 days after pesticide application | 7 days after pesticide application | 14 days after pesticide application | 21 days after pesticide application | 30 days after pesticide application |
| 6 | 50 | 98.58 | 96.69 | 99.28 | 95.86 | 94.62 |
| 14 | 100 | 99.24 | 96.92 | 97.14 | 96.30 | 95.71 |
| | 50 | 99.61 | 98.90 | 99.08 | 98.57 | 97.35 |
| | 100 | 99.65 | 98.31 | 98.93 | 96.95 | 97.19 |
| Spirodiclofen | 100 | 91.09 | 80.88 | 80.88 | 72.63 | 73.60 |
| Pyridaben | 100 | 80.24 | 61.51 | 61.51 | 51.62 | 56.60 |

In order to discover new phenyl sulfide derivatives with higher acaricidal activity, it is not obvious to find that the acaricidal activity is greatly influenced by the position of substituent on the benzene ring, which is at the fifth position of the benzene in (4-fluoro-2-substituted phenyl)-2,2,2-trifluoroethyl sulfide (sulfoxide or sulphone) structure. Compounds with substituents at the intersite position have the best activity, and the substituents nitro, methylthio or $SCH_2CF_3$, at the intersite position are preferred. The new substituted phenyl sulfide compounds of the present invention show high acaricidal activity at 10 mg/L and exhibit excellent acaricidal activity at 1.25 mg/L as well, and are safe for crops.

Other compounds of general formula I in the present invention disclosure, prepared by the methods mentioned above, showed corresponding bioefficacy.

The invention claimed is:

1. A substituted phenyl sulfide compound of formula I:

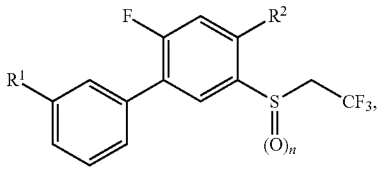

I wherein:

$R^1$ is nitro;

$R^2$ is halogen, cyano, or $C_1$-$C_4$ alkyl; and n is 0.

2. The compound according to claim 1, wherein:

$R^1$ is nitro;

$R^2$ is selected from fluorine, chlorine, and methyl;

n is selected from 0.

3. The compound according to claim 2, wherein:

$R^1$ is nitro;

$R^2$ is chlorine or methyl; and n is 0.

4. The compound according to claim 3, wherein:

$R^1$ is nitro;

$R^2$ is methyl; and n is 0.

5. An acaricidal composition, comprising the compound of claim 1 as an active ingredient and agriculturally acceptable carrier, wherein a weight percentage of the active ingredient in the composition is 0.1-99%.

6. A method for controlling spider mites, comprising applying an effective amount of the acaricidal composition according to claim 5 to a habitant of mites.

7. The method according to claim 6, where the mites are one or more selected from spider mites, *Panonychus ulmi, Panonychus citri*, and eggs thereof.

8. The method according to claim 6, wherein the concentration of the active ingredient in the acaricidal composition is 0.625 mg/L to 1.25 mg/L.

9. The method according to claim 6, wherein the concentration of the active ingredient in the acaricidal composition is 50 mg/L to 100 mg/L.

* * * * *